(12) United States Patent
Foody et al.

(10) Patent No.: US 8,252,568 B2
(45) Date of Patent: Aug. 28, 2012

(54) PROCESS FOR PRODUCING A PRETREATED FEESTOCK

(75) Inventors: Pat Foody, Hudson (CA); Vijay Anand, Brossard (CA)

(73) Assignee: Iogen Energy Corporation, Ontario (CA)

(*) Notice: Subject to any disclaimer, the term of this patent is extended or adjusted under 35 U.S.C. 154(b) by 210 days.

(21) Appl. No.: 12/722,591

(22) Filed: Mar. 12, 2010

(65) Prior Publication Data

US 2010/0190226 A1 Jul. 29, 2010

Related U.S. Application Data

(62) Division of application No. 11/661,863, filed as application No. PCT/CA2005/001374 on Sep. 9, 2005, now Pat. No. 7,709,042.

(60) Provisional application No. 60/609,098, filed on Sep. 10, 2004.

(51) Int. Cl.
*C12P 7/14* (2006.01)
*C12P 7/06* (2006.01)
*C12P 7/08* (2006.01)
*C12P 7/16* (2006.01)

(52) U.S. Cl. ......... 435/162; 435/161; 435/163; 435/165

(58) Field of Classification Search .................. 435/161, 435/162, 163, 165
See application file for complete search history.

(56) References Cited

U.S. PATENT DOCUMENTS

| | | | |
|---|---|---|---|
| 2,828,081 A | 3/1958 | Collins et al. | |
| 3,554,453 A | 1/1971 | Thale et al. | |
| 4,237,226 A | 12/1980 | Grethlein | |
| 4,436,028 A | 3/1984 | Wilder | |
| 4,525,172 A | 6/1985 | Eriksson | |
| 4,543,881 A | 10/1985 | Anderson | |
| 4,683,814 A | 8/1987 | Plovanich et al. | |
| 4,728,044 A | 3/1988 | Duill et al. | |
| 5,451,296 A | 9/1995 | Pikulin et al. | |
| 5,571,703 A | 11/1996 | Chieffalo et al. | |
| 5,735,916 A | 4/1998 | Lucas et al. | |
| 6,036,818 A | 3/2000 | Odmark | |
| 6,090,595 A | 7/2000 | Foody et al. | |

FOREIGN PATENT DOCUMENTS

| | | |
|---|---|---|
| GB | 473708 | 10/1937 |
| WO | 02/070753 | 9/2002 |

OTHER PUBLICATIONS

Sassner, et al., "Stem Pretreatment of Salix with and without SO2 Impregnation for Production of Bioethanol", Appl. Biochem. Biotech., vol. 121-124 (2005) 1101-17.

Millett, et al, "Physical and Chemical Pretreatments for Enhancing Cellulose Saccharification", Biotechnol. & Bioeng. Symp. No. 6, (1976) 125-53.

Grethlein, H. "Chemical Breakdown of Cellulosic Materials", J. Appl. Chem. Biotechnol., vol. 28 (1978) 296-308.

*Primary Examiner* — Herbert J Lilling
(74) *Attorney, Agent, or Firm* — Fitzpatrick, Cella, Harper & Scinto

(57) ABSTRACT

A process for producing ethanol from a pretreated feedstock is provided. The feedstock is selected from grasses, cereal straws, stover, and combinations thereof, and least about 80% of the feedstock has a particle length of between about 2 cm and about 40 cm. This process comprises wetting the feedstock in liquid, pressing the wet feedstock through one roll press or a series of roll presses to remove at least a portion of water and soluble substances from the wetted feedstock and to shear the feedstock to produce feedstock particles of a size suitable for pumping at a solids concentration of about 8% to about 20% when slurried. At least one roll press, or at least one roll press in the series of roll presses comprises rolls with circumferential v-shaped grooves. The pressed feedstock particles are slurried to produce a slurried feedstock having a consistency of between about 8% and about 20%, and the slurried feedstock pumped into a pretreatment reactor. Dilute acid pretreatment of the slurried feedstock is carried out at a temperature of 160° C. to 280° C.

28 Claims, 7 Drawing Sheets

PROCESS FOR PRODUCING A PRETREATED FEESTOCK

This application is a divisional of application Ser. No. 11/661,863 filed Mar. 5, 2007, which is itself a 371 National stage application of International application No. PCT/CA2005/001374, filed Sep. 9, 2005, which claims benefit of U.S. provisional application No. 60/609,098, filed Sep. 10, 2004, each of which are incorporated by reference herein.

The present invention relates to a process for producing a pretreated feedstock, more particularly to a process for producing cellulose-containing pretreated feedstock.

BACKGROUND OF THE INVENTION

Fuel ethanol is currently produced from feedstocks such as cornstarch, sugar cane, and sugar beets. However, the production of ethanol from these sources cannot expand much further due to limited farmland suitable for the production of such crops and competing interests with the human and animal food chain. The use of fossil fuels, with the associated release of carbon dioxide and other products, in the conversion process is a negative environmental impact of the use of these feedstocks The production of fuel ethanol from cellulose-containing feedstocks, such as agricultural wastes, grasses, forestry wastes, and sugar processing residues has received much attention due to the availability of large amounts of these inexpensive feedstocks and the cleanliness of ethanol as a fuel compared to gasoline. In addition, a byproduct of the cellulose conversion process, lignin, can be used as a fuel to power the cellulose conversion process, thereby avoiding the use of fossil fuels. Studies have shown that, taking the entire cycle into account, the use of ethanol produced from cellulose generates close to nil greenhouse gases.

The cellulosic feedstocks that may be used for ethanol production include agricultural wastes such as corn stover, wheat straw, barley straw, canola straw, and soybean stover. Grasses such as switch grass, miscanthus, cord grass, and reed canary grass may also be used.

Cellulose consists of a crystalline structure that is very resistant to breakdown, as is hemicellulose, the second most prevalent component of these feedstocks. The conversion of cellulosic fibers to ethanol requires liberating cellulose and hemicellulose from lignin or increasing the accessibility of cellulose and hemicellulose within the cellulosic feedstock to cellulase enzymes, depolymerizing hemicellulose and cellulose carbohydrate polymers to free sugars and, fermenting the mixed hexose and pentose sugars to ethanol.

The feedstock is conveyed into the plant and the feedstock particles are typically reduced to a desired size suitable for handling in subsequent processing steps.

Among well-known methods used to convert cellulose to sugars is an acid hydrolysis process involving the use of steam and acid at a temperature, acid concentration and length of time sufficient to hydrolyze the cellulose to glucose (Grethlein, 1978, J. Appl. Chem. Biotechnol. 28:296-308).

An alternative method of cellulose hydrolysis is an acid prehydrolysis (or pre-treatment) followed by enzymatic hydrolysis. In this sequence, the cellulosic material is first pretreated using the acid hydrolysis process described above, but at milder temperatures, acid concentration and treatment time. This pretreatment process is thought to increase the accessibility of cellulose within the cellulosic fibers for subsequent enzymatic conversion steps, but results in little conversion of the cellulose to glucose itself. In the next step, the pretreated feedstock is adjusted to an appropriate temperature and pH and then submitted to enzymatic conversion by cellulase enzymes.

The hydrolysis of the cellulose, whether by acid or by cellulase enzymes, is followed by the fermentation of the sugar to ethanol, which is then recovered by distillation.

The efficient conversion of cellulose from cellulosic material into sugars and the subsequent fermentation of sugars to ethanol are faced with major challenges regarding commercially viability. In particular, the feedstock particles are often too large to be efficiently handled or processed. One desirable type of handling system that requires small particles is pumping. In dry processes, for particle size reduction, water is not added to the feedstock. Dry processes which include grinding, milling or crushing, require large amounts of power that adds to the cost of the overall process. Furthermore, dry processing to a small particle size suitable for pumping is unlikely to be successful for feedstocks having high or variable moisture contents. Some feedstocks containing 20% or higher moisture frequently blind the milling equipment, and it does not provide a sustainable or suitable size reduction. The alternatives are wet grinding processes or apparatus that make use of equipment such as using refiners or hydropulpers; however, wet grinding also requires costly equipment and high power usages. Furthermore, wet grinding produces a material that is very dilute and costly to handle and process.

A second problem with the conversion process is that the acid requirement in the pretreatment process is very high. Many feedstocks, such as straws and corn stover, contain a high native alkalinity that requires the addition of 0.5% to 6% w/w (of the feedstock) of sulfuric acid to achieve an efficient hydrolysis of the hemicellulose and exposure of the cellulose surface area. A significant amount of this acid serves to offset the alkalinity inherent within the feedstock. This high acid usage not only increases the cost of the process, but can also cause degradation of the xylose and other products during the pretreatment process.

WO 02/070753 (Griffin et. al.) describes a leaching process comprising contacting the feedstock with water for at least two minutes to leach out the salts, protein, and other impurities, followed by removal of the water and soluble compounds. The process of Griffin et. al. removes alkali from lignocellulosic feedstocks, thereby decreasing the acid requirement for pretreatment. Griffin requires particle size reduction, but the processes consume a high level of power and, in combination with the equipment required to carry out the leaching process, result in increased overall process costs.

The use of presses for dewatering biomass is known in the art. For example, U.S. Pat. No. 4,436,028 (Wilder) describes the use of a hammermill to greatly reduce particle size followed by a two-roll mill exerting severe pressure to decrease the moisture content of waste material. Similarly, U.S. Pat. No. 4,525,172 (Eriksson) teaches the dewatering of biomass using presses with sieving drums. However, these methods do not result in the grinding, shearing, or particle size reduction of the biomass during pressing or dewatering. This results in high capital and operating costs without achieving the necessary particle size reduction.

U.S. Pat. No. 4,543,881 (Anderson) discloses an apparatus for dewatering peat which includes an outer tubular roll and a smaller inner roll received in the outer roll. The smaller inner roll rotates so that its outer surface moves along the inner surface of the outer tubular roll, thereby compressing peat placed between the rolls to effect dewatering. By operating the rolls at different speeds, shear forces and compression forces act on the peat. However, the purpose of the roll compression apparatus is to dewater the peat and not to reduce particle size.

U.S. Pat. No. 2,828,081 (Collins) describes the use of roll presses to separate cork from phloem tissue on dry bark. A dried cork-rich fraction is passed through a differential speed roller mill that, through shearing action, breaks up the cork aggregates without substantially reducing the cork particle size. This process is not designed for size reduction of the particles of the material. As well, bark is not suitable for ethanol production.

In order to address the need for further particle size reduction of biomass, various approaches have been taken. For example, U.S. Pat. No. 6,036,818 (Odmark) describes a pulp dewatering device having two rolls through which the pulp is pressed (a roll press). As the pulp passes through the rolls, a doctor blade disintegrates and guides the pulp out of the press, and the pulp is further disintegrated by a screw disintegrator. U.S. Pat. No. 5,451,296 (Pikulin), teaches the use of a thickening unit (e.g. a twin roll press) to remove excess liquid from low consistency pulp. The resulting high consistency pulp is conveyed to a comminuting unit, such as a fJuffer, to generate pulp particles of 10 mm or less. The roll presses used in either U.S. Pat. No. 6,036,818 or U.S. Pat. No. 5,451,296 do not convey grind, shear, or reduce the particle size of the pulp. Rather, additional equipment is required to accomplish particle size reduction, thus increasing both equipment and energy costs for the overall process.

U.S. Pat. No. 4,728,044 (Duill and Brummer) discloses a system for grinding and drying damp initial material. The starting material is pre-comminuted by a hammer mill while being dried with hot gas. Following further drying in a rising main, the material is further comminuted in the nip between the rollers of a high-pressure roll. The finished material emerges as dried and ground raw material. Although the process is suitable for the grinding and drying of materials such as raw cement meal, cement clinker, ore, coal and the like, the further processing of feedstock to produce ethanol is not addressed. None of the suitable feedstocks for ethanol production are mentioned.

U.S. Pat. No. 4,237,226 (Grethlein) describes milling of dry oak wood chips in a laboratory setting using a Wiley mill to produce a sawdust-like product. The ground chips pass through a screen of 60 mesh, then are slurried in water at a ratio of water to solids of 18.5 to 1 by weight prior to feeding the slurry to a continuous pretreatment reactor. The Wiley mill is not suited for use with fiber with over 20% moisture content, and exhibits high power consumption. Furthermore, there is no disclosure of commercial-scale equipment that may be used to carry out these processing steps.

Millett et al. (Biotechnol. & Bioeng. Symp. No. 6 (1976) 125-153) disclose several physical treatments for the preparation of feedstocks, including dry ball milling, wet ball milling and vibratory ball milling. The production of fine particles by dry ball milling adds substantially to the cost of the process, while wet ball milling for 72 hours increased the digestibility of cellulose by rumen bacteria. However, 72 hours is not a practical treatment time in a production process, and there is no mention of subsequent pretreatment or enzymatic hydrolysis. Vibratory ball milling of dry spruce and aspen chips for 30 minutes at 220° C. was found to increase the rate of enzymatic hydrolysis. However, this treatment adds considerable expense to the process.

U.S. Pat. No. 3,554,453 (Thale et al.) discloses an apparatus for shredding fibrous articles such as groundwood, compressed webs and flat pieces of sulfite and semi-chemical pulp. The apparatus contains a shredding roller and a holding roller, each with interdigitating toothed discs for shredding the fibrous material as it advances between the rollers. The action of the toothed discs on the rollers generates defibered material and does not result in pressing of the material.

U.S. Pat. No. 4,683,814 (Plovanich et al.) discloses an apparatus and a dry process for dewatering cellulosic biomass, which utilizes a pair of smooth opposed rolls operating at different speeds. Due to the differential roller speeds, the compressed biomass is heated, which results in additional moisture removal, and particle size reduction. Furthermore, moisture collects on the roll rotating at the higher rate and compressed material adheres to the roll rotating at the lower rate. This allows moisture to be collected from the roll rotating at the higher speed and compressed material to be collected from the roll rotating at the lower speed. Although the process provides an effective means for the dewatering of biomass, the process of Plovanich et al. only removes a minority of the alkalinity of the feedstock. Moreover, Plovanich et al. do not teach the production of a cellulosic feedstock having a particle size suitable for pumping.

The process for extracting sugar from sugar cane feedstocks is well known. This involves washing the sugar cane surface to remove impurities, coarsely chopping the stalks into smaller pieces, and crushing the sugar cane pieces in a series of roller mills to extract the juice. The juice is collected from the presses and further processed to produce sugar. The residue from the cane stock after juice extraction (bagasse) is usually burned at the mill.

In order for a continuous pretreatment of cellulosic feedstocks to be economically and commercially viable, the pretreatment system must be amenable to the pretreatment of a variety of feedstocks; the alkalinity of the feedstock must be reduced from its native levels, so as to decrease the acid requirements and degradation of sugar products by acid; and the feedstock particle size must be reduced, without requiring excessive power or capital equipment, such that the particles can be pumped in aqueous medium.

The development of such a system remains an important component of the overall process to convert cellulosic feedstocks to glucose and subsequently to ethanol.

SUMMARY OF THE INVENTION

The present invention relates to a process for producing a pretreated feedstock, more particularly to a process for producing cellulose-containing pretreated feedstock.

It is an object of the present invention to provide a process for producing a pretreated feedstock with improved efficiency.

The present invention provides a process for producing a pretreated feedstock, the process comprising the steps of:
  a) providing a feedstock selected from the group consisting of grasses, cereal straws, stover, and combinations thereof, wherein at least about 80% of the feedstock has a particle length of between about 2 and about 40 cm;
  b) wetting the feedstock in an aqueous stream to about 0.25 to about 10 times the maximum water holding capacity of the feedstock to produce a wet feedstock;
  c) pressing the wet feedstock through one roll press or a series of roll presses to remove at least a portion of water and soluble substances from the wet feedstock and to shear the wet feedstock to produce a pressed feedstock having a particle size, such that when the pressed feedstock is slurried to produce a slurried feedstock, the slurried feedstock is capable of being pumped at a solids concentration of about 8% to about 20%, wherein the one roll press, or one or more than one roll press in said series, comprises rolls with circumferential v-shaped grooves, and wherein the pressed feedstock has a consistency of at least about 35% dry solids after passing through a nip point in the one roll press or a nip point in one or more than one roll press in said series;

d) slurrying the pressed feedstock particles to produce a slurried feedstock having a solids concentration of about 8% to about 20% and pumping the slurried feedstock into a pretreatment reactor; and e) carrying out dilute acid pretreatment of the slurried feedstock, at a temperature of about 160° C. to about 280° C. to produce the pretreated feedstock.

The present invention is also directed to the method as just described, wherein, after the step of slurrying (step d), the feedstock is pretreated at a temperature of about 170° C. to about 260° C. and at pH of about 0.8 to about 2.0 for a period of 0.1 to 30 minutes. Furthermore, the pretreated feedstock may be hydrolyzed by cellulase enzymes to produce glucose, which may subsequently be fermented to ethanol. Prior to the step of pressing (step c), the feedstock may be partially leached.

The present invention is also directed to the invention as described above, wherein, in the step of providing (step a), the cereal straw is selected from the group consisting of wheat straw, barley straw, rice straw, canola straw, and oat straw, and the stover is selected from the group consisting of corn stover and soybean stover. Preferably, in the step of providing (step a), at least about 80% of the feedstock has a particle length of between about 2 and about 30 cm.

The present invention is also directed to the invention as described above, wherein, in the step of pressing (step c), the one roll press or one or more than one roll press in the series creates additional shear to reduce the feedstock particle size, and wherein the additional shear is created by a difference in diameter or a difference in speed of the rolls in the one roll press, or in one or more than one roll press in the series.

Preferably, the series of roll presses comprises 3 roll presses, although 2 roll presses can be used as well.

The present invention is also directed to the invention as described above, wherein a series of presses are used, and wherein the step of wetting (step b) comprises countercurrent washing of the feedstock with pressate collected from at least one roll press in the series.

The present invention is also directed to the invention as described above, wherein, in the step of wetting (step b), the liquid is at a temperature of between about 20° C. and about 95° C., or between about 30° C. and about 85° C.

The present invention is also directed to the invention as described above, wherein, in the step of slurrying (step d), the slurried feedstock has a consistency of between about 10% and about 18% dry solids, or between about 12% and 15% dry solids. Preferably, after the step of pressing (step c) and before the step of slurrying (step d), the pressed feedstock has a consistency of at least about 35% dry solids. In the step of slurrying (step d), at least about 70%, 80% or 89% of the feedstock particles may be 2.4 cm or less in length.

The present invention is also directed to the invention as described above, wherein, in the step of pressing (step c), one or more than one other press or one or more than one other dewatering device is used in combination with the one roll press or the series of roll presses, wherein the one or more than one other press or the one or more than one other dewatering device is not a roll press. If other press types or dewatering devices besides roll presses are used in combination with the one roll press or the series of roll presses, the consistency of the feedstock after pressing the wetted feedstock is preferably at least about 35% dry solids.

Furthermore, the present invention is also directed to the invention as described above, wherein the process is a continuous process with continuous feeding of the feedstock and continuous withdrawal of the pretreated feedstock.

The wet treatment process of the present invention overcomes the disadvantages of the prior art, as it requires much less power input than a dry grinding process. The invention also mitigates the risk of blinding dry milling equipment with feedstock having a high moisture content. Furthermore, the presses require much less power input and cost much less than other wet grinding equipment, such as refiners or hydropulpers. The process of the present invention produces a feedstock that is pumpable with a minimal amount of aqueous solution.

In addition, by using a wet process, a significant portion of the salts, alkali, and protein are removed from the feedstock. This decreases the acid requirement and potentially increases the xylose yield. These benefits are consistent with those achieved by WO 02/070753 (Griffin) using a leaching of the feedstock, but without the contact times and equipment used in a leaching process.

Therefore, the invention offers significant advances in the production of sugar from lignocellulosic feedstocks.

This summary of the invention does not necessarily describe all required features of the invention.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1A:
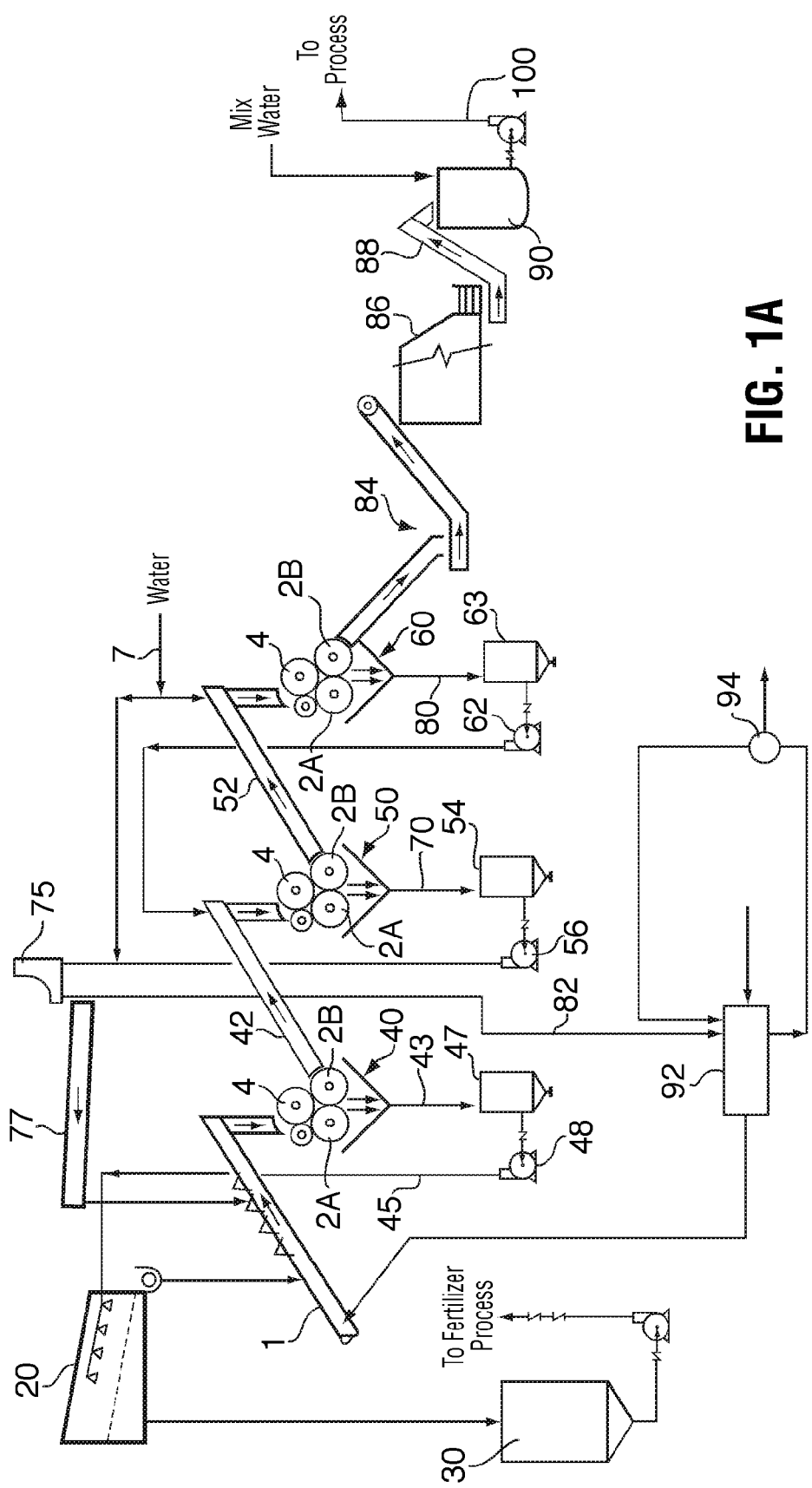
FIG. 1A shows an example of a feedstock handling system in accordance with the present invention.

The present invention relates to a process and apparatus for handling wet feedstock, more particularly to a process and apparatus for handling wet cellulose-containing feedstock.

The present invention provides a process that allows for the crushing and shearing of feedstock and the removal of much the soluble salts, protein, sugars, alkaline compounds, and organic acids from the feedstock. The wetted feedstock undergoes pressing using one roll press, or a series of roll presses. The result is that the particle size is reduced and moisture is pressed out of the wetted feedstock. Soluble components thus released may be collected during pressing and shearing of the feedstock and the pressed and sized feedstock can then be subjected to pretreatment or pretreatment combined with subsequent treatment steps for its conversion to sugars. The process may be used as a continuous process, so that the feedstock may be fed, and prepared feedstock withdrawn, in a continuous manner. However, the process may also be used for batch processing. The process of the present invention removes potential inhibitors from the feedstock, and also decreases the acid requirement during pretreatment.

The present invention provides a process for producing a pretreated feedstock comprising:
a) providing a feedstock selected from the group consisting of grasses, cereal straws, stover, and combinations thereof, wherein at least 80% of the feedstock has a particle length of between about 2 and about 40 cm;
b) wetting the feedstock in an aqueous stream to about 0.25 to about 10 times the maximum water holding capacity of the feedstock to produce a wet feedstock;
c) pressing the wet feedstock through one or a series of roll presses to remove at least a portion of water and soluble substances from the wet feedstock and to shear the wet feedstock to produce a pressed feedstock having a particle size such that, when the pressed feedstock is slurried to produce a slurried feedstock, the slurried feedstock is capable of being pumped at a solids concentration of about 8 to about 20%,
wherein the one roll press, or one or more than one roll press in said series, comprises rolls with circumferential v-shaped grooves, and
wherein the pressed feedstock has a consistency of at least about 35% dry solids after passing through a nip point in the one roll press or a nip point in one or more than one roll press in said series;
d) slurrying the pressed feedstock particles to produce a slurried feedstock having a solids concentration of about 8% to about 20% and pumping the slurried feedstock into a pretreatment reactor; and
e) carrying out dilute acid pretreatment of the slurried feedstock at a temperature of about 160° C. to about 280° C. to produce the pretreated feedstock.

The process of the invention is effective on a wide variety of feedstocks, including: (1) stover, such as corn stover or soybean stover; (2) cereal straws, such as wheat straw, barley straw, canola straw, oat straw, and rice straw; (3) grasses such as switch grass, miscanthus, cord grass, and reed canary grass; and any combination thereof. These feedstocks are available in large quantity at low cost and contain high levels of carbohydrates, which correspond to a high potential ethanol yield.

The feedstock is usually conveyed into the ethanol plant in bales or other convenient form. The bales may be coarsely broken up to create particles that can be handled by the one roll press or the series of roll presses using any method known in the art. For example, the feedstock may be broken up in a coarse size reduction process using a hammer mill, a rotary shredder, shear shredder, knife hog, tub grinder, wood chipper-like device, or any other device that reduces the particle size of the entering solids. The size of the reduced feedstock is suitable for handling in the system of the present invention, i.e., at least 80% of the reduced feedstock has a particle length of about 2 to about 40 cm, or any amount therebetween. Preferably, at least 80% of the feedstock may have a length of about 2 to about 30 cm, or about 4 to about 25 cm, or any amount therebetween.

In the process of the present invention, the feedstock is wetted in an aqueous stream prior to pressing. The aqueous stream can be any suitable liquid that wets the feedstock and thereby permits it to be pressed by the one or more roll presses. For example, the liquid may be water, mill water, or recycled wash liquor (pressate) obtained from earlier feedstock processing. In the latter case, wetting of the feedstock may comprise counter-current washing of the roll presses with the resulting liquor used to wet the feedstock upon entry into the plant.

The feedstock may be wetted using any method known in the art. For example, the feedstock may be wetted by spraying the liquid onto the feedstock, by immersion in a tank of liquid, or by passing the feedstock through a tank of liquid.

The amount of liquid used is chosen so as to be enough to wet the feedstock and provide some extra liquid for the removal of impurities, but is not in such excess as to produce dilute streams that increase handling expenses. The optimal amount of liquid required to adequately wet the feedstock will vary based on the physical properties of the feedstock and the feedstock particle size. An acceptable amount of water is about 0.25 to about 10 times the maximum water holding capacity of dry feedstock, or any amount therebetween. For example, the amount of water added may be about 0.25, 0.5, 1.0, 1.5, 2.0, 3.0, 4.0, 5.0, 6.0, 7.0, 8.0, 9.0 and 10 times the maximum water holding capacity of dry feedstock, or any amount therebetween. More preferably, the amount of water added is about 1.5 to about 3 times the maximum water holding capacity of dry feedstock, or any amount therebetween. The maximum water holding capacity of a feedstock is determined by measuring the weight of water which is absorbed by a known mass of loosely packed feedstock until the point at which additional water added to the feedstock is free water. This point is measured as the point in which the water forms a thin continuous layer over the feedstock. In determining the maximum water holding capacity of a feedstock, it is preferable that the feedstock is mechanically disrupted into particles of about the same size. Furthermore, as would be evident to a person skill in the art, it is preferred that the maximum water holding capacity of a feedstock be determined on a loosely packed and not tightly packed feedstock. As an example, if 1 kg of feedstock (dry basis) holds 4000 g of water, the maximum water holding capacity of the feedstock is 4000 g/kg. The acceptable amount of water is then 1000 g to 40,000 g per kg feedstock.

Alternatively, an acceptable ratio of water to solids may be from about 2.5:1 to about 100:1, by weight, or any amount therebetween. More preferably the ratio of water to solids is from about 2.5:1 to about 25:1, by weight, or any amount therebetween. For example the ratio of water to solids may be about 2.5:1, 5:1, 7.5:1, 10:1, 12.5:1, 15:1, 17.5:1 20:1, 22.5:1 or 25:1, by weight, or any amount therebetween. A typical ratio of liquid to feedstock is about 2.5:1 to about 10:1, or any amount therebetween, for example 2.5:1, 5:1, 7.5:1, or 10:1 by weight.

The addition of water followed by pressing removes a significant amount of the alkalinity and nitrogen and potassium from the feedstock. This decreases the acid usage in pretreatment and may increase the xylose yield.

The feedstock may be wetted as part of a sand removal process or a leaching process prior to pressing. Sand removal has the advantage of preserving the roll presses from abrasion due to the presence of sand on the feedstock. For sand removal, water is combined with the feedstock at the ratio as described above, i.e., about 0.25 to about 10 times the maximum water holding capacity of dry feedstock, or any amount therebetween, more preferably about 1.5 to about 3 times the maximum water holding capacity of dry feedstock, or any amount therebetween. In this process, feedstock wetting may be carried out over a rotating drum with a screen, or some other equipment familiar in the art. The filtrate, which contains sand, water, and soluble impurities, is settled to remove the sand, while the liquor can be reused to wash feedstock newly conveyed to the plant. In a non-limiting example, sand removal is carried out by introducing the sand-containing filtrate to a hydroclone.

Regardless of whether sand is removed or not, the temperature of the liquid for wetting the feedstock may be any temperature in the range of about 20° C. to about 95° C., for example a temperature of 20, 25, 30, 35, 40, 45, 50, 55, 60, 65, 70, 75, 80, 85, 90 or 95° C., or any amount therebetween. In general, warmer temperatures may result in a more efficient extraction of soluble components by the liquid. The temperature range of the liquid may be about 30° C. to about 85° C., or any temperature therebetween.

The wetted feedstock is then subjected to size reduction. This is accomplished by conveying the feedstock through one or a series of roll presses. Each roll press used in the process of the present invention may be a roll press that is commercially available (e.g. from Edwards Engineering Corp. Houston Tex.; Bundaberg Foundry Engineers Ltd., Bundaberg Australia; or Fulton Iron and Manufacturing LLC, St. Louis Mo.), and may comprise a suitable number of rolls, for example, but not limited to, three (see for example FIG. IB) or four rolls (see FIG. IA; roll presses 40, 50 and 60). Additionally, the roll press may be a modified roll press as described in more detail below.

The present invention may use either one, or more than one roll press in series, to deliver adequate particle size reduction. For example, the process of the present invention may use from one to seven roll presses, or any amount therebetween; for example, 1 or 2, 3, 4, 5, 6 or 7 roll presses in series, may be used. In a more specific example, the process uses two to four roll presses in series. Preferably, the process uses two or three roll presses in series. The roll presses in the series may be arranged one behind the other in succession (see FIG. IA), or other process equipment may be interposed between the presses.

Furthermore, one or more than one other types of presses or dewatering devices could be used in combination with the one roll press or the series of roll presses. Such press types or dewatering devices may include, but are not limited to, belt presses, filter presses, screw presses and centrifuges.

Without wishing to be limiting in any manner, each roll press (3) may have three or four rolls (FIG. IB). In this configuration, three of the four rolls are set in a triangular pattern with first and second lower rolls (2A and 2B, respectively) at the bottom, side by side, and a third top roll (4) at the top between the bottom rolls. Preferably, the first and second rolls (2A, 2B) are supported by bearing journals fixed to the supporting frame of the roll press, and the top roll (4) may be mounted on a set of guide plates that allows the roll (4) to move up and down. The top roll (4) may also have hydraulic cylinders mounted on each end for application of the crushing, shearing or crushing and shearing force between the top and bottom rolls. If the roll press comprises four rolls, then the fourth roll acts as a feed roller. A series of roll presses, each comprising four rolls, is shown in FIG. IA.

Referring to FIG. IB, in a non-limiting example, during operation of the press (3), the wet feedstock is crushed twice, once between the top roll (4) and the first lower roll (2A) and then between the top roll (4) and the second lower roll (2B). The feed opening (8A) between the top roll (4) and the first lower roll (2A) and the discharge opening (8B) between the top roll (4) and the second lower roll (2B) are each set to a desired clearance. The feedstock is guided through the press by guidance device (9).

The rolls of the press may be constructed of any suitable material, for example, but not limited to, stainless steel. The dimensions of each roll may vary as required, but may, for example, which is not to be considered limiting, be from about 0.75 m to about 4 m long, or any value therebetween, with a diameter of from about 0.45 m to about 2 m, or any value therebetween.

Figure 1B:
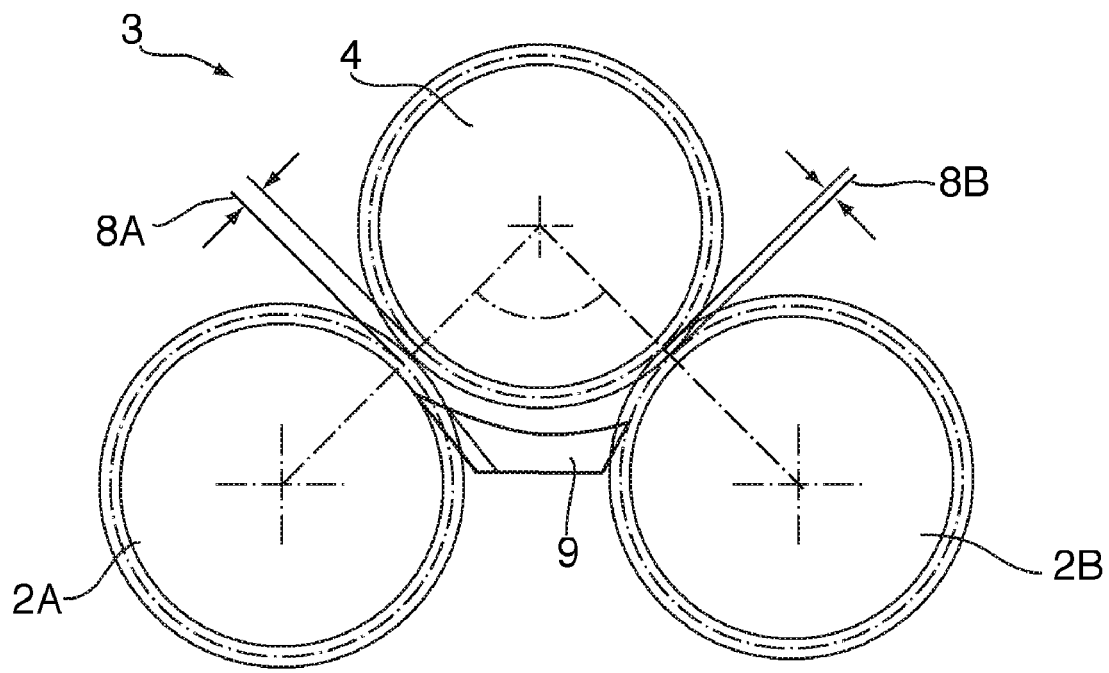
FIG. 1B shows a roll press comprising three rollers.
Figure 1C:
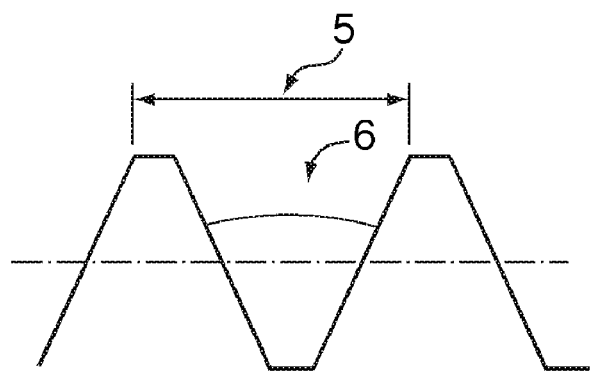
FIG. 1C shows a cross section of the tooth profile that may be present on the outer surface of the rollers in the roll press.

One or more than one of the presses comprise press rolls with circumferential grooves having a "vee" shape (v-shape) cross-section cut into the outer surface of each roll (6; FIG. 1C). The provision of roll presses with such circumferential grooves enhances drainage and shearing of the wet feedstock. The moisture content of the wet feedstock is reduced, thereby removing soluble substances and increasing the consistency of the feedstock. The shearing of the feedstock by the grooves allows for efficient particle size reduction to produce a pumpable feedstock.

The spacing (5) between the grooves may be from about 1.0 cm to about 10.0 cm, or any value therebetween, and the groove depth may be from about 1.0 cm to about 10.0 cm, or any value therebetween. The top roll (4) is set such that the grooves of the three rolls mesh with each other, but the rolls are not in contact (8A and 8B; FIG. 1B). The clearance between the roll nip points may be from about 0.0001 cm to about 0.1 cm, or any value therebetween. Meshing of the grooves (6) and crushing load between rolls provides the majority of shearing action.

It should be appreciated that, if a series of presses are utilized, in order to produce the required particle size reduction, it is not necessary that all of the presses contain rolls with circumferential grooves. For example, it is contemplated that adequate shearing and moisture reduction could be achieved if one or more of the presses comprise rolls having circumferential grooves, while the remaining roll presses have smooth rolls.

The rolls of the press apply pressure to the feedstock as it is fed through the roll press(es). The pressure applied to the rolls may be adjusted as necessary to create additional shear to reduce particle size. A suitable pressure range for removal of the pressate and reduction of feedstock particle size is in the range of about 2400 to about 3000 psi or any value therebetween. For example, the press nip pressure may be of about 2400, 2500, 2600, 2700, 2800, 2900 or 3000 psi, or any value therebetween.

The roll presses may be modified to increase the degree of milling of the feedstock. Increased milling of the feedstock may be achieved by using rolls of varying diameter rotating at the same speed. The difference in diameter may be of about 1.2 cm to about 20.0 cm, or any value therebetween; more specifically, the diameters may differ by about 1.5 cm to about 10.0 cm, or about 1.5 to about 2.5 cm, or any amount therebetween. Alternatively, rolls of the same diameter may be used, but the rolls are rotated at different speeds. In this case, the difference in speed between the rollers may be from 0% to about 10%, or any value therebetween; in a more specific example, the speeds may differ by about 3.5% to about 10%, or any value therebetween. The use of rollers of different diameters, rollers rotating at different speeds, or the use of both rollers having different diameters and rotating at different speeds results in efficient feedstock particle size reduction, and may result in the use of fewer roll presses to achieve the desired feedstock particle size. Furthermore, the gap between the rolls may be adjusted as desired to create additional shear.

As a result of passing through one roll press or a series of roll presses, the feedstock particle size is reduced to a size suitable for handling. The particles are of a size such that, when the pressed feedstock is subsequently slurried, the resulting slurry can be pumped at a dry solids concentration of about 8 to about 20%, or any amount therebetween. Preferably, the particles are of a size such that the slurried feedstock can be pumped at a solids concentration of about 10% to about 18% dry solids or any range therebetween, or about 12% to about 15% dry solids, or any range therebetween. Preferably, the feedstock is of a size appropriate to be slurried and pumped using medium consistency pumps (such as a Sulzer MC® Pump). Once the feedstock exits one or a series of roll presses, the majority of the feedstock particles may be about 10 cm or less in length. Preferably, at least about 70%, 80% or 89% of the feedstock particles are of a length of 2.4 cm or less. For example from about 70% to about 89%, or any amount therebetween, of the feedstock particles are of a length from about 0.05 to about 2.4 cm or any amount therebetween.

As set forth above, pressing of the wetted feedstock results in an increase in the consistency of the feedstock. If only one roll press is used, the consistency of the feedstock is at least about 35% dry solids, or from about 35% to about 95% or any amount therebetween dry solids, after passing through one nip point of the press. For example, the consistency of the feedstock may be from about 35% to about 60%, or any amount therebetween If a series of roll presses are used, then the consistency of the dry solids is at least about 35%, or from about 35% to about 60%, or from about 35% to about 95%, or any amount therebetween, dry solids, after passing through a nip point of at least one (i.e., one or more than one) roll press in the series. By way of illustration, and with reference to FIG. IB, the consistency of the feedstock after passing between the top roll (4) and the first bottom roll (2A) or after passing between the top roll (4) and the second bottom roll (2B) is at least about 35%. Preferably, after the step of pressing and before the step of slurrying, the consistency of the feedstock is at least about 35%. For example, with reference to FIG. IA, the consistency of the feedstock is at least about 35% after exiting the third roll press, for example at 60.

It should be appreciated that, after the moisture content of the wetted feedstock is reduced in a roll press, or other type of press or dewatering device which is optionally used in combination with the one press or series of roll presses, the moisture content of the feedstock may be increased prior to entering a downstream press or dewatering device. For example, an aqueous stream may be added to the discharge of the upstream press, the inlet of a downstream press, or dewatering device, or any point in between.

As a further step after pressing or slurrying, the feedstock may be subjected to additional leaching. This is carried out by contacting the feedstock with water for a period of time adequate to allow a portion of the soluble components in the feedstock to dissolve, followed by separating at least a portion of the aqueous solution from the feedstock solids.

Following pressing, the feedstock is slurried in water. The amount of water added to the feedstock is typically chosen as the minimum that allows the feedstock to be pumped. This is typically to achieve a consistency or solids concentration of about 8% to about 20%, or any value therebetween. For example, the consistency or solids concentration may be about 8, 10, 12, 14, 15, 16, 18, or 20%, or any value therebetween. Preferably, the reduced feedstock is slurried to produce a feedstock slurry having a consistency of about 10 to 18%, or about 12 to 15%, or any range therebetween.

Alternatively, the amount of water added to the feedstock may be from about 2.5 to about 10 parts water per part solid, by weight, or any value therebetween. For example, the ratio between water to solid, by weight, may be from about 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1 or 10:1 or any amount therebetween. For example which is not to be considered limiting, the reduced feedstock is slurried in 5 or 6 parts water per part solids (5:1 or 6:1).

The slurried feedstock is then subjected to a dilute acid pretreatment process. The pretreatment process converts hemicellulose, or a portion thereof, to sugars and may convert a portion of the cellulose to sugar. A non-limiting example of such a treatment includes steam explosion, as described in U.S. Pat. No. 4,461,648 (Foody; which is incorporated herein by reference). Generally, dilute acid pretreatment conditions for lignocellulosic feedstocks comprise a temperature in the range of about 160° C. to about 280° C., or any amount therebetween, for example 160, 170, 180, 190, 200, 210, 220, 230, 240, 250, 260, 270 or 280° C., for a period of about 0.1 to about 30 minutes, or any amount therebetween, including 0.1, 0.5, 1, 5, 10, 15, 20, 25, or 30 min, and at a pH of about 0.8 to about 2.0, or any amount therebetween, for example a pH of 0.8, 1, 1.2, 1.4, 1.6, 1.8 or 2.0. The low pH for pretreatment requires the addition of acid to the feedstock. The acid used for pretreatment may be any type of suitable acid known in the art, including, but not limited to, sulfuric acid, sulfurous acid, or phosphoric acid. Sulfuric acid is preferred due to its low cost and, following recovery, its use in fertilizer in the form of sulfate salts. Prominent pretreatment processes carried out with dilute acid include those described by Grethlein (U.S. Pat. No. 4,237,226) and in Sassner et al. (*Appl. Biochem. Biotech,* 2005, 121-124:1 101-1 117), which are incorporated herein by reference.

The pretreated feedstock may then be subjected to enzymatic hydrolysis with cellulase enzymes, to convert the cellulose to glucose. Without wishing to be bound by theory, the pretreatment increases the susceptibility of the feedstock to hydrolysis by cellulase enzymes. Cellulase enzymes can typically tolerate a range of pH of about 3 to 7; therefore, the pretreated feedstock is generally neutralized prior to enzymatic hydrolysis. Adjustment of the pH after pretreatment can be carried out using ammonia gas, ammonia dissolved in water (ammonium hydroxide), sodium hydroxide, lime, sodium carbonate or potassium hydroxide. A pH more favorable to the cellulase enzymes is, for example, within the range of about 4.5 to about 5.0, or any value therebetween, for example a pH of 4.5, 4.6, 4.7, 4.8, 4.9 or 5.0. The pH-adjusted, pretreated feedstock can then be subjected to enzymatic hydrolysis using cellulase enzymes.

By the term "cellulase enzymes", "cellulase", or "enzymes", it is meant enzymes that catalyse the hydrolysis of cellulose to products such as glucose, cellobiose, and other cellooligosaccharides. Cellulase is a generic term denoting a multienzyme mixture, produced by a number of microorganisms, comprising exo-cellobiohydrolases (CBH), endoglucanases (EG) and β-glucosidases (βG). Among the most widely studied, characterized, and commercially produced cellulases are those obtained from fungi of the genera *Aspergillus, Humicola,* and *Trichoderma,* and from the bacteria of the genera *Bacillus* and *Thermobifida*. The cellulase enzymes may be produced by genetic engineering techniques, which are well-known to those of skill in the art. In a non-limiting example, the pretreated feedstock described above may be submitted to hydrolysis by cellulase enzymes produced by *Trichoderma*.

In a preferred embodiment, the sugar is fermented to ethanol. Fermentation may be carried out by yeast, bacteria or other microbes, or an enzyme mixture, capable of fermenting the product stream to a desired efficiency and yield. In a preferred embodiment, the fermentation is carried out using a genetically engineered yeast, for example, but not limited to, *Saccharomyces* or *Pichia*, or bacteria, for example, but not limited to, *Zymomonas* or *E. coli* capable of fermenting the pentose sugars xylose, arabinose, or a combination thereof, in addition to the hexose sugars glucose, mannose, galactose, or a combination thereof. Alternatively, the sugar in the product stream is fermented to lactic acid. Those skilled in the art are familiar with the requirements in fermentation of sugar to produce ethanol, organic acids, or sugar alcohols.

With reference to FIG. IA, a non-limiting example of the overall process system is shown. The feedstock, for example bales of wheat straw are shredded and wetted with water at 0.25 to 10 times the maximum water holding capacity of the wheat straw. The feedstock is washed over an inclined rotating drum with a screen (20). Sand and liquor containing soluble solids pass through the screen. The stream of sand and liquor is sent to a hydroclone or settling tank (30) to remove the sand. The liquor may be reused to wash incoming feedstock, or processed for other uses.

The screened, wetted feedstock is moved onto a first conveyor belt (1). The feedstock may be wetted by liquor from the pressate (43, 70 or both) of the first or second or both, roll press (40, 50), respectively. The wet feedstock is conveyed to the first roll press (40), where it is crushed and pressed. The pressate (43), which contains small particles and liquor, may be sent (via line 45) to the inclined rotating drum with a screen (20) via first pump (48). Prior to being sent to the rotating drum (20), the pressate (43) may be sent to a first swirl tank (47). The pressate solids are recovered and combined with the feedstock feeding into the first roll press (40). The liquor, which contains soluble protein, sugars, and salts, may be collected and potentially used as a byproduct. The liquor can also be sent for further processing, for example, but not limited to, protein recovery and concentration.

The once-pressed solids are conveyed by a second conveyor (42) to the second roll press (50). The solids are wetted by pressate (80) from a third roll press (60). The wet solids pass through roll press (50). The pressate (70), which contains small particles and liquor, is fed by second pump (56) to a solids removal screen (75) to recover solids. The pressate (70) may pass through a second swirl tank (54) before being introduced to the solids removal screen (75). The pressate solids recovered by the screen (75) are fed to a conveyor (77) and introduced to the first conveyor (1) feeding the first roll press (40). The liquor (82) may be introduced to a washer liquor tank (92) and pumped to a clarifier (94) to remove fines. The clarified liquor (96) may then be fed back to the first conveyor (1).

The twice-pressed solids are conveyed along a third conveyor (52) toward a third roll press (60). The solids are wetted with process or imbibition water (7). The pressate (80) from third press (60) contains small particles and liquor. This pressate (80) containing small particles is added to the feedstock solids feeding the second roll press (50) via third pump (62). This permits leaching of the feedstock with a three-stage countercurrent washing/wetting of the feedstock. Optionally, the pressate (80) may pass through a third swirl tank (63).

At the conclusion of the third press, the feedstock particles have been sheared to a size suitable for pumping. The crushed fiber from the third roll press (60) is then sent by conveyor system (84) to a holding bin (86) where it is held for a fixed period of time. The crushed fiber is then introduced via conveyor (88) to a mix tank (90) where it is slurried to produce a feedstock slurry having a consistency of 8% to 20%, or 10% to 18%, or 12% to 15%, or any amount therebetween. Alternatively, the crushed fiber from the third roll press (60) may be slurried in about 4.5 to about 8 parts water per part solid, by weight, or any amount therebetween, for example about 4.5, 4.8, 5.0, 5.2, 5.4, 5.6, 5.8, 6.0, 6.2, 6.4, 6.6, 6.8, 7.0, 7.2, 7.4, 7.6, 7.8, or 8.0 parts water per part solid, or any amount therebetween, for example about 5 parts.

The slurry is then submitted to further processing (100), which involves a step of pretreatment in a pretreatment reactor. In the pretreatment reactor, the slurry is subjected to dilute acid prehydrolysis, and the resulting pretreated slurry is then submitted to enzymatic hydrolysis to convert the cellulose to sugars as described earlier.

The present invention will be further illustrated in the following examples.

EXAMPLES

Example 1

Use of Roll Press System to Decrease Particle Size of Wheat Straw

Initial size reduction of wheat straw was performed using a wood chipper-like device. The average length of the straw was reduced to about 15 cm. The chopped straw was stored until required for press trials, with about ⅓ in a covered truck bed, and the remainder in an outdoor bin. Heavy rain was experienced for two days during the trial.

The mill was of a four-roll type, with a "floating" hydraulically damped top roll. The clearance between the roll nip points was set to 0.0001" (one ten thousandth of an inch). The rolls were of stainless steel construction, 0.76 m (30") long, with a diameter of 0.457 m (18"). The rolls were circumferentially grooved, with a spacing of 1.3 cm (0.5") between the grooves. The groove depth was not recorded. The mill was driven via a 480 V, 74 A, 60 hp, 1775 rpm electric motor. The motor was connected to a gearbox, but the gear reduction ratio and the final roll rpm were not stated. The mill was instrumented with needle gauges showing the motor amps and the nip pressure between the rolls.

Straw was manually loaded into a stainless steel wire mesh basket. A sample of the feed straw was obtained from each basket for initial moisture content measurement, particle size analysis and chemical composition. The basket had a capacity of 1 cubic meter, sufficient for 50 kg of loosely packed straw. The exact weight of each basket used was recorded. The basket was immersed in approximately 4900 liters of water in a 5500 liter tank for 20 minutes. The initial and final water level were recorded for each basket and a sample of the vat contents obtained to estimate the amount of water removed with the straw, and to allow calculation of the amount of straw materials dissolved per basket. After the 20 minute soak, the basket was withdrawn from the vat and allowed to drain for about 10 minutes.

A sample of the soaked and drained straw was taken from each basket for moisture content analysis. Approximately half of the basket (~25 kg oven dried straw) was manually loaded on a 1.5 ft by 8 ft conveyor belt, and the belt hoisted to the feed hopper on the mill. The speed of the belt was manually controlled to maintain a level in the feed hopper. The average time required to feed the straw on the belt was measured for five trials. A sample of the pressed straw was taken for moisture content measurement, particle size analysis and chemical composition. A sample of mill pressate was obtained for dissolved and undissolved solids analysis. The process was repeated for the second half of the basket.

Prior to the start of the double pass material, a gas powered water pump was obtained, and the leaching vat was emptied and refilled. Single pass material was again prepared by processing 8 baskets of straw through a single mill pass, with the pressed material stored in the plant overnight. The single pass material was then reloaded into baskets, soaked and drained, as previously described, and run through the mill for a second pass.

The triple pass material was produced in a similar fashion.

The single, double, and triple pass straw was analyzed for pump testing. Samples of the feed and pressed straw were also submitted for inorganic and nitrogen analysis. The leachate and pressate were analyzed for dissolved and total solids. In addition, the straw was analyzed for moisture content and particle size.

The particle size was measured in two ways. For the initial wheat straw sample and a sample from each of the mill passes, 100 randomly chosen fibers were measured with a ruler, and the average length calculated. Secondly, portions of the straw were oven dried and a 20 gram sample of the oven dried straw were subjected to particle size analysis using a set of five standard sieves, with the amount of straw retained on each sieve weighed. The mass of material retained on each screen was recorded. Three samples each of the coarsely chopped, single, double, and triple milled material were analyzed, and the results averaged for each type of material.

Medium Consistency (MC®) pump testing was also performed on single, double, and triple pass cane press straw. The double and triple pass straw was combined for analysis. The tests were conducted by adding the wet, pressed straw to a known volume of water in the standpipe. The total water volume in the standpipe was calculated as the sum of the initial water volume, the seal water leakage rate, and the volume of water in the wet straw. Samples of straw were taken from each drum of material and analyzed for solids content. The drums were weighed, so that the dry mass of straw could be calculated. The liquid to solids ratio was then calculated as the total water volume divided by the oven dry weight of straw mass.

Power Consumption

The required time for feeding 25 kg oven dried straw was consistently between 20 to 35 seconds, and the average measured time from five trials was 30 seconds. The dry fiber throughput of the test mill is estimated to be 2.5-3 tonnes per hour. While feeding straw to the mill, the motor current draw averaged about 55 A, which is 75% of the rated full load, and the nip pressure increased by only 100-200 psig, or about 8%, over the no load value. The true upper throughput boundary is thus not known.

Using a motor current draw average of 55 A, with a range from 50-57 A, and a motor voltage of 480 V, a feed time of 30 seconds (0.0083 hrs) for 25 oven dried kg of straw, the specific power consumption is calculated as:

(55 A*480 V)*(1 KW/1000 W)*0.0083 hr/0.025 tonne straw=8.8 KWhr/tonne straw.

Note that the Fulton mill has a higher throughput and a lower energy requirement than the currently used hammermill. The largest mills that are currently in service were driven by 1200 hp motors, and were capable of processing 9000 tonnes of sugar cane per day.

Particle Length Distribution

Figure 2:
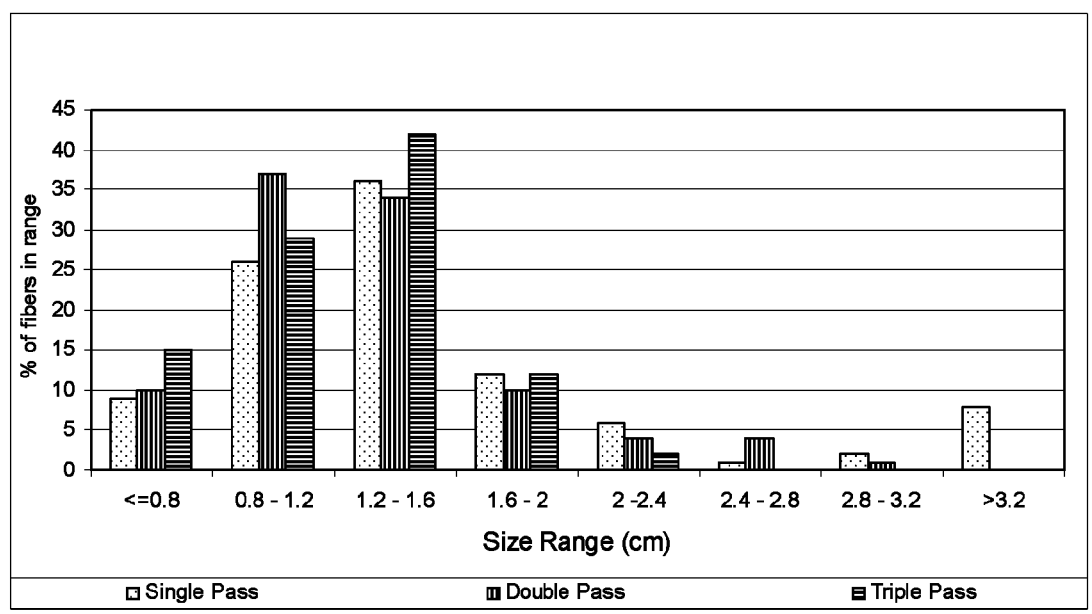
FIG. 2 shows results of an analysis of wheat straw particle length following processing according to the present invention. Particle length measurements were determined following coarse chopping after a single (left bar), double (middle bar) or triple (right bar) pass through the mill. 100 fibers were randomly selected and manually measured with a ruler to estimate the particle length distribution.

The results of the particle length distribution are shown graphically in FIG. 2 for the pressed wheat samples. From observation of the press while in operation, it was apparent that a fraction of the straw is bypassing the grooved section of the rolls, and was escaping the mill prematurely along the sides of the rolls. This could be avoided by installation of steel scrapers along side the rolls. It is this fraction that is responsible for the oversized material. The fraction of oversized material is reduced by successive mill passes without dramatically changing the average fiber length.

It should be noted that in analysis of particle length distribution using sieves, the straw is separated on the basis of the particle diameter, not length. While the sizes do not represent the true average fiber length of the material, previous work has shown a correlation between the average particle length and the sieve size for hammermilled straw. Visual inspection of the sieved samples showed that a similar trend held for the pressed straw material—larger particles were retained on the larger mesh screens, while the shorter particles were retained on the smaller screens. The results are presented in FIG. 3, which provides an indication of the distribution of fiber sizes, and the amount of fines that are produced.

Figure 3:
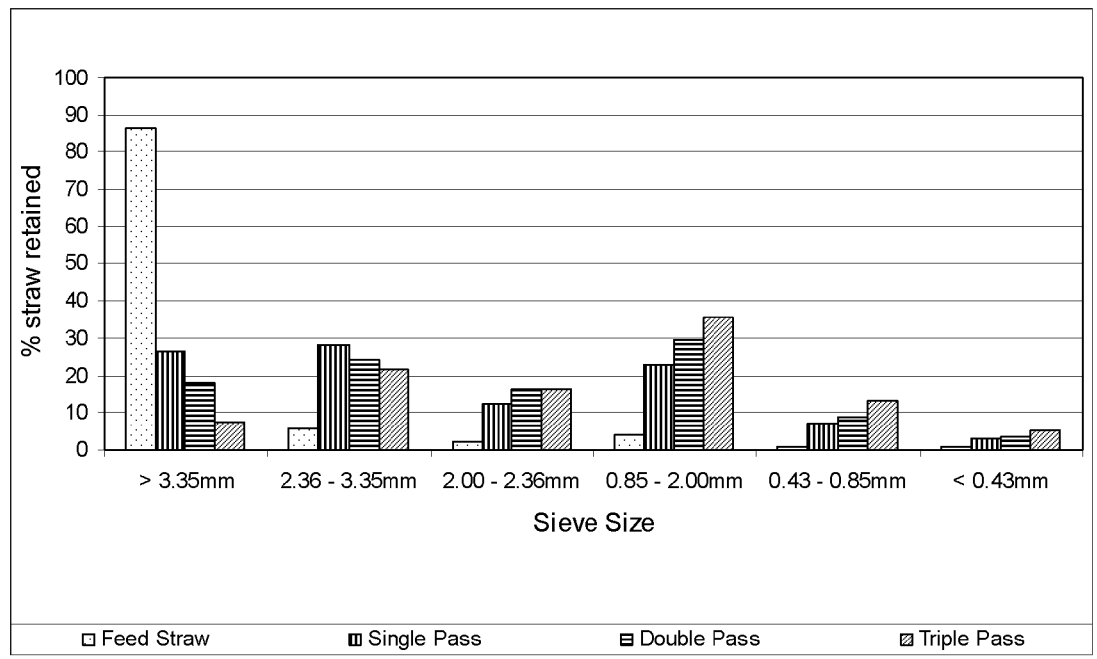
FIG. 3 shows results of an analysis of wheat straw particle size following processing according to the present invention. Particle size is determined using standard square mesh sieves. The sieves separate the straw on the basis of the particle diameter, not length. Three samples each of the coarsely chopped (left bar), single (left-middle bar), double (right-middle bar), and triple (right bar) milled material were passed through sieves of varying sizes, and the results averaged for each type of material.

The results shown in FIGS. 2 and 3 indicate that successive mill passes reduce both the amount of oversize material and the amount of material retained on the largest sieve. Additionally, the average particle size tends towards the roll groove spacing of 1.3 cm. Also, the fines content, classified as material smaller than 0.85 mm, is only slightly increased by successive passes through the mill.

The production of milled wheat straw fines is not entirely addressed by FIG. 2 and FIG. 3, since some fraction of the fines will be carried by the mill pressate. Samples of the pressate were analyzed for undissolved solids—that is, wheat straw fines—but the size distribution of the solids was not determined. Visual inspection of the mill pressate indicated the majority of the wheat straw particles in the pressate were very small, on the order of 0.2 cm or less. The weight percent of undissolved solids in the mill pressate is presented in Table 1.

TABLE 1

Weight percent undissolved solids in mill pressate

| Sample | Wt % Undissolved |
|---|---|
| Single pass | 0.85 |
| Double pass | 1.20 |
| Triple pass | 1.70 |

Using the moisture content of the feed and pressed straw, the total amount of pressate generated can be calculated. When combined with the data on the undissolved solids in the pressate, the total amount of fines lost in the pressate can be calculated on a dry straw basis. This is presented in Table 2.

TABLE 2

Percent of feed straw lost as fines in the pressate

| Sample | % feed as fines in pressate |
|---|---|
| Single pass | 2.0 |
| Double pass | 2.5 |
| Triple pass | 3.9 |

Fines recovery is a standard procedure for the sugar cane industry, and the normal method is to screen the mill pressate.

Soluble Component Analysis

Figure 4:
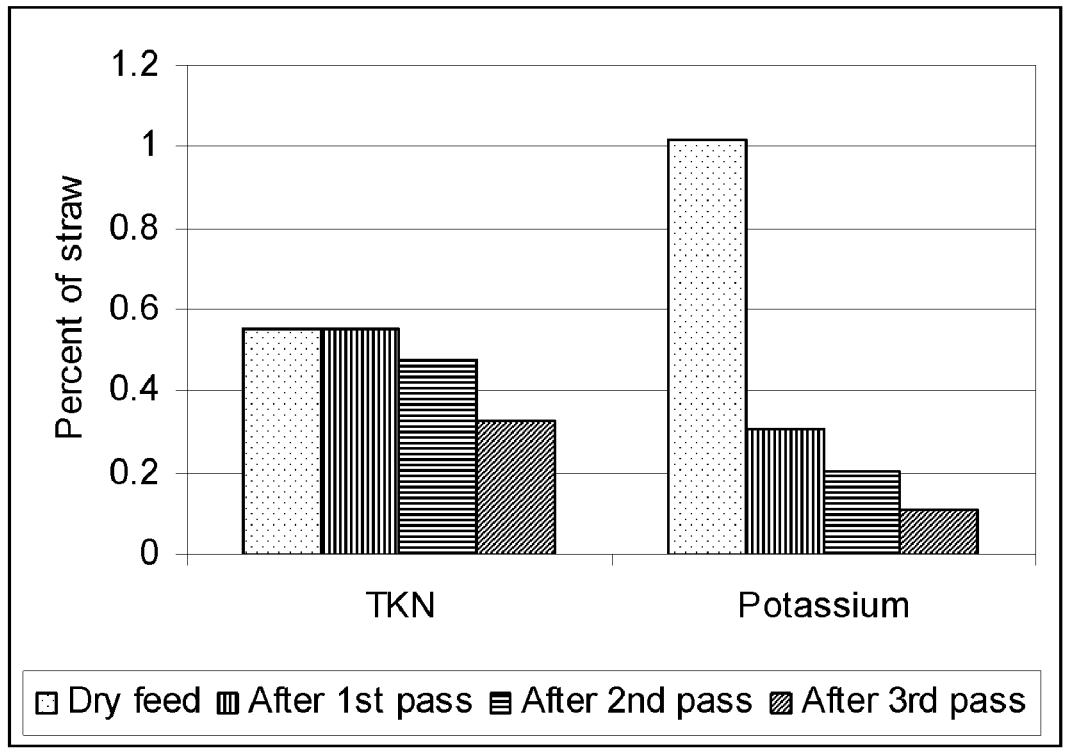
FIG. 4 shows the amount of water-soluble potassium and total nitrogen (total Kjedahl nitrogen; TKN) found in the dry feedstock (left bar) or after single (left-middle bar), double (right-middle bar) or triple (right bar) passes through the mill. The dissolved components were determined before and after pressing and are expressed as a percent of the original content.

The composition of the non-structure components of wheat straw is shown in FIG. 4.

The soluble potassium salts show a 90% decrease due to leaching. The nitrogen content, which is related to the protein content of the straw, is reduced by about 40% after three passes through the cane press. The silica, ash and calcium content of the straw are unaffected by the leaching and pressing operation, under the conditions of this test.

Pumpability Testing

Figure 5:
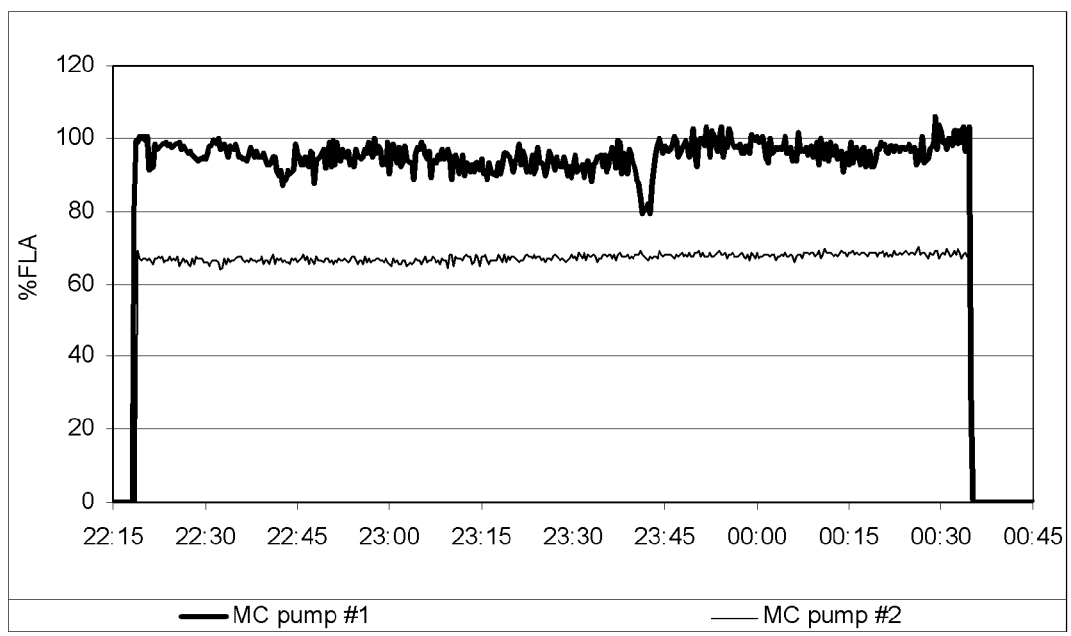
FIG. 5 shows the medium consistency (MC®) pump current during testing of single pass wheat straw.

Medium Consistency (MC®) pump testing of single, double, and triple pass cane press straw was performed. For the single pass material, the final liquid to solids ratio achieved was 6.1:1. The test was halted when all the single pass straw had been consumed by the test. The only data that is available from active instruments during this test are the MC pump amperages, the standpipe level reading, and the discharge pressure from MC pump #1 (P20408). Of these, the standpipe level is only of interest in the calculation of the liquid to solids ratio, and the MC pump #1 discharge pressure is manually controlled at approximately 65 psig by varying the pump speed and the gate valve on the MC pump #1 recirculation line. The amperage for MC pump #1 is controlled by these same means, with a target value close to 100% full load amps. The only independent parameter is the amperage for MC pump #2. The current draw for the two MC pumps during this trial is presented in FIG. 5. The current for MC pump #2 increased by only 2%, from 66 to 68% full load amps (% FLA), during this test.

Figure 6:
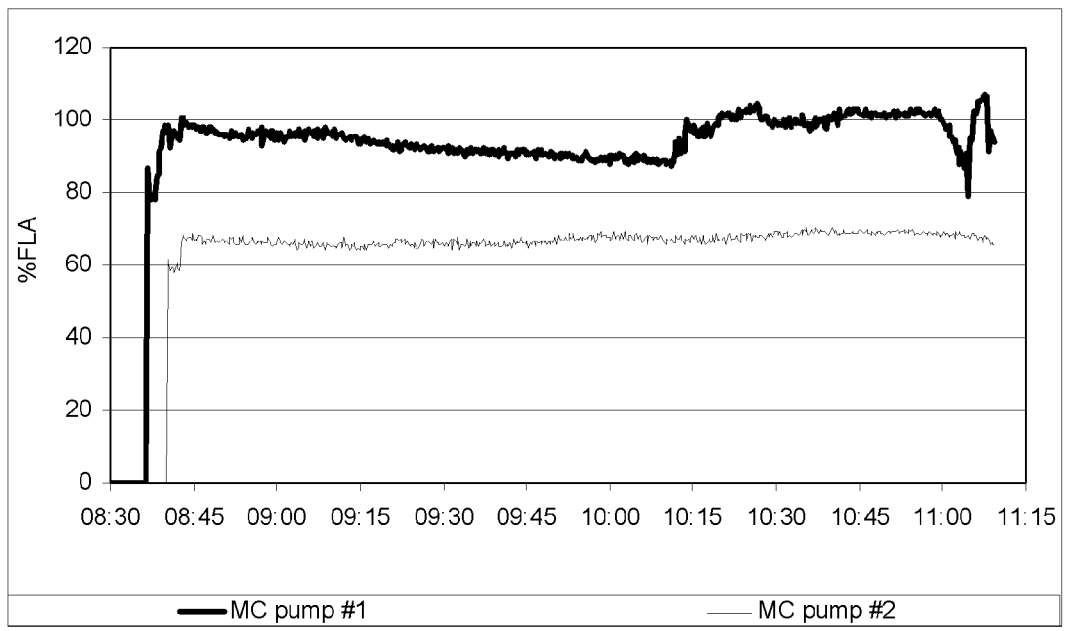
FIG. 6 shows the MC® pump current during testing of combined double and triple pass wheat straw.

A similar test was conducted using the combined double and triple pass material. The test was halted at a final liquids-to-solids ratio of 5.9:1 due to an overflow in the standpipe. Again, it may have been possible to push to higher solids consistencies. The current draw for the two MC pumps is presented in FIG. 6. MC pump #2 shows the same 2% current increase from 66 to 68% FLA.

Summary

Roll press test work was conducted using a Fulton press. The equipment was evaluated on the basis of power consumption, throughput, and particle size reduction. Approximately 300 kg each of single, double and triple pass material was prepared. Chemical analysis of the straw was conducted to determine the endogenous salts removed during the pressing operation.

The wheat straw particle size was reduced from an initial coarsely chopped average length of approximately 15 cm to approximately 70% being 1.5 cm or less during the first pass, and with the remaining 30% of the straw having lengths up to 6 cm. Successive passes through the press reduced the percentage of oversized material, but only slightly reduced the median size of particles produced. There was a 3-fold increase in the amount of fines collected in the mill pressate from singly to triply pressed material.

Pump testing of the pressed straw showed behavior similar to hammer milled wheat straw. The final liquid to solids obtained was on the order of 6:1. The pumpability of the material seemed independent of the number of cane press passes in that single and double pass material behaved similarly.

The average amount of dissolved material in the vat leachate and mill pressate was only 2.5% of the initial dry straw mass. Readily soluble potassium salts were removed; calcium, ash, and silica were reduced by less than 10%. The total Kjeldahl nitrogen (TKN) was reduced by about 40%.

The estimated throughput of the press used for the testing was 2.5 to 3 tonnes oven-dried straw per hour. This rate was based on a feed time of about 30 seconds for 25 kg of straw, but the mill may have been run below capacity. The specific energy consumption for press operation was calculated to be on the order of 9 kWhr/tonne of straw. The amount of power required to chop the straw to a similar particle length with a hammer mill is 70 kWhr/tonne.

The pressed straw had an average moisture content of 45%. This value was not affected by the number of passes through the mill. Previous testing produced a value of 43% solids with an applied pressure of 2500 psi in a hydraulic press, similar to the average recorded cane press nip pressure of 2900 psi recorded for this trial.

Example 2

Use of Roll Press System with Enhanced Shear to Optimize Particle Size of Wheat Straw Initial size reduction of wheat straw is done using a wood chipper-like device. The average length of the straw is reduced to about 15 cm. The chopped straw is stored until required for press trials.

The mill is of a four-roll type, with a "floating" hydraulically damped top roll. The clearance between the roll nip points is set to about 0.0001" (one ten thousandth of an inch). The rolls are of stainless steel construction, 0.76 m (30") long, with a diameter of 0.457 m (18") or 0.432 m (17"). The rolls are circumferentially grooved, with a spacing of 1.3 cm (0.5") between the grooves. The mill is driven via a 480 V, 74 A, 60 hp, 1775 rpm electric motor. The mill is instrumented with needle gauges showing the motor amps and the nip pressure between the rolls.

The shear produced by the rolls of the press is increased by either a) using a top roll with a diameter of 0.432 m (17") compared to 0.457 m (18") for the bottom rolls, or b) driving the top roll at a speed approximately 5% faster than that of the bottom rolls. Either of these situations results in a speed differential between the rolls, leading to increased shear applied to the feedstock.

Straw is manually loaded into a stainless steel wire mesh basket. A sample of the feed straw is obtained from each basket for initial moisture content measurement, particle size analysis and chemical composition. The basket has a capacity of 1 cubic meter, sufficient for 50 kg of loosely packed straw. The exact weight of each basket used is recorded. The basket is immersed in approximately 4900 liters of water in a 5500 liter tank for 20 minutes. The initial and final water level are recorded for each basket and a sample of the vat contents obtained to estimate the amount of water removed with the straw, and to allow calculation of the amount of straw materials dissolved per basket. After the 20 minute soak, the basket is withdrawn from the vat and allowed to drain for about 10 minutes.

A sample of the soaked and drained straw is taken from each basket for moisture content analysis. Approximately half of the basket (~25 kg oven dried straw) is manually loaded on a 1.5 f by 8 f conveyor belt, and the belt hoisted to the feed hopper on the mill. The speed of the belt is manually controlled to maintain a level in the feed hopper. The average time required to feed the straw on the belt is measured for five trials. A sample of the pressed straw is taken for moisture content measurement, particle size analysis and chemical composition. A sample of mill pressate is obtained for dissolved and undissolved solids analysis. The process is repeated for the second half of the basket.

Prior to the start of the double pass material, the leaching vat is emptied and refilled. Single pass material is again prepared by processing 8 baskets of straw through a single mill pass. The single pass material is then reloaded into baskets, soaked and drained as previously described and run through the mill for a second pass.

The triple pass material is produced in a similar fashion.

Samples of the feed and pressed straw are submitted for inorganic and nitrogen analysis. The leachate and pressate are analyzed for dissolved and total solids. The straw is also analyzed for moisture content and particle size. The particle size is measured in two ways. For the initial wheat straw sample and a sample from each of the mill passes, 100 randomly chosen fibers are measured with a ruler, and the average length calculated. Secondly, portions of the straw are oven dried and a 20 gram sample of the oven dried straw are subjected to particle size analysis using a set of five standard sieves, with the amount of straw retained on each sieve weighed. The mass of material retained on each screen is recorded. Three samples each of the coarsely chopped, single, double, and triple milled materials are analyzed, and the results averaged for each type of material.

Results obtained using a) a top roll with a diameter of 0.432, and b) a top roll speed approximately 5% faster are similar to those set out in Example 1.

All citations are hereby incorporated by reference.

The present invention has been described with regard to one or more embodiments. However, it will be apparent to persons skilled in the art that a number of variations and modifications can be made without departing from the scope of the invention as defined in the claims.

The embodiments of the invention in which an exclusive property of privilege is claimed are defined as follows:

1. A process for producing ethanol comprising:
   a) providing a feedstock selected from the group consisting of grasses, cereal straws, stover, and combinations thereof, wherein at least 80% of the feedstock has a particle length of between about 2 and about 40 cm;
   b) wetting the feedstock in an aqueous stream at about 0.25 to about 10 times the maximum water holding capacity of the feedstock to produce a wet feedstock;
   c) pressing the wet feedstock through one roll press or a series of roll presses to remove at least a portion of water and soluble substances from the wet feedstock and to shear the wet feedstock to produce a pressed feedstock having a particle size such that, when the pressed feedstock is slurried to produce a slurried feedstock, the slurried feedstock is capable of being pumped at a dry solids concentration of about 8% to about 20%,
   wherein the one roll press, or one or more than one roll press in said series, comprises rolls with circumferential v-shaped grooves, and
   wherein the pressed feedstock has a consistency of at least about 35% dry solids after passing through a nip point in the one roll press or a nip point in one or more than one roll press in said series;
   d) slurrying the pressed feedstock particles to produce a slurried feedstock having a dry solids concentration of about 8% to about 20% and pumping the slurried feedstock into a pretreatment reactor; and
   e) carrying out dilute acid pretreatment of the slurried feedstock, at a temperature of 160° C. to 280° C. to produce the pretreated feedstock;
   f) hydrolyzing the pretreated feedstock using cellulase enzymes to produce glucose; and
   g) fermenting the glucose to produce ethanol.

2. The process of claim 1, wherein, in the step of providing (step a), the cereal straw is wheat straw, barley straw, rice straw, canola straw, or oat straw.

3. The process of claim 1, wherein, in the step of providing (step a), the stover is corn stover or soybean stover.

4. The process of claim 1, wherein sand is removed from the feedstock prior to pressing (step c).

5. The process of claim 1, wherein, in the step of wetting (step b), the aqueous stream is water or a water-based solution.

6. The process of claim 1, wherein, in the step of providing (step a), the feedstock has a particle length of between about 2 and about 30 cm.

7. The process of claim 6, wherein, in the step of slurrying (step d), the slurry is pumped to the pretreatment reactor and subsequently pretreated at a temperature of 170° C. to 260° C. at pH 0.8 to 2.0 for a period of 0.1 to 30 minutes to produce the pretreated feedstock.

8. The process of claim 1, wherein the feedstock is partially leached prior to the step of wetting (step b) or pressing (step c).

9. The process of claim 1, wherein, in the step of pressing (step c), a series of three roll presses are used.

10. The process of claim 1, wherein, in the step of wetting (step b), the liquid is at a temperature of between about 20° C. and about 95° C.

11. The process of claim 9, wherein, in the step of wetting (step b), the liquid is at a temperature of between about 30° C. and about 85° C.

12. The process of claim 1, wherein, in the step of pressing (step c), the one roll press or one or more than one roll press in said series exerts a pressure of about 2400 psi to about 3000 psi on the feedstock.

13. The process of claim 1, wherein, in the step of slurrying (step d), at least 70% of the feedstock particles are 2.4 cm or less in length.

14. The process of claim 13, wherein, in the step of slurrying (step d), at least 80% of the feedstock particles are 2.4 cm or less in length.

15. The process of claim 14, wherein, in the step of slurrying (step d), at least 89% of the feedstock particles are 2.4 cm or less in length.

16. The process of claim 1, wherein, in the step of pressing (step c), the one roll press or one or more than one roll press in said series creates additional shear to reduce the feedstock particle size.

17. The process of claim 16, wherein the additional shear is created by a difference in diameter of the rolls of the one roll press or at least one roll press in said series.

18. The process of claim 17, wherein the diameter of the rolls of the one roll press, or one or more than one roll press in said series, varies by about 1.2 cm to about 20 cm.

19. The process of claim 16, wherein the additional shear is created by a difference in speed of the rolls of the one roll press or one or more than one roll press in said series.

20. The process of claim 19, wherein the speed of the rolls of the one roll press, or one or more than one roll press in said series, varies by about 3.5% to about 10%.

21. The process of claim 1, in which a series of presses are used, and wherein the step of wetting (step b) comprises countercurrent washing of the feedstock with pressate collected from one or more than one roll press in said series.

22. The process of claim 1, wherein, in the step of slurrying (step d), the slurried feedstock has a consistency of between about 10% and about 18% dry solids.

23. The process of claim 22, wherein the slurried feedstock has a consistency of between about 12% and about 15% dry solids.

24. The process of claim 1, wherein, in the step of pressing (step c), a series of two roll presses are used.

25. The process of claim 1, wherein, after the step of pressing (step c) and before the step of slurrying (step d), the pressed feedstock has a consistency of at least about 35% dry solids.

26. The process of claim 1, wherein, in the step of pressing (step c), one or more than one other press or one or more than one other dewatering device is used in combination with the one roll press or the series of roll presses, wherein the one or more than one other press or the one or more than one other dewatering device is not a roll press.

27. The process of claim 26, wherein, after the step of pressing (step c) and before the step of slurrying (step d), the pressed feedstock has a consistency of at least about 35% dry solids.

28. The process of claim 1, wherein the process is a continuous process with continuous feeding of the feedstock and continuous withdrawal of the pretreated feedstock.

* * * * *